US010206445B2

(12) United States Patent
Kim

(10) Patent No.: US 10,206,445 B2
(45) Date of Patent: Feb. 19, 2019

(54) HAIRWEAR HAVING AUXILIARY DEVICE FOR HEAD SHAPING OR SPACE FORMATION

(71) Applicant: SSECRET WOMAN CO., LTD, Daejeon (KR)

(72) Inventor: Yeoung-Hyu Kim, Daejeon (KR)

(73) Assignee: SSECRET WOMAN CO., LTD, Daejeon (KR)

( * ) Notice: Subject to any disclaimer, the term of this patent is extended or adjusted under 35 U.S.C. 154(b) by 0 days.

(21) Appl. No.: 14/889,222

(22) PCT Filed: Nov. 27, 2014

(86) PCT No.: PCT/KR2014/011482
§ 371 (c)(1),
(2) Date: Nov. 5, 2015

(87) PCT Pub. No.: WO2015/083981
PCT Pub. Date: Jun. 11, 2015

(65) Prior Publication Data
US 2016/0262480 A1    Sep. 15, 2016

(30) Foreign Application Priority Data
Dec. 6, 2013 (KR) .................. 10-2013-0151906

(51) Int. Cl.
*A45F 5/00* (2006.01)
*A41G 3/00* (2006.01)
(Continued)

(52) U.S. Cl.
CPC ......... *A41G 3/0058* (2013.01); *A41G 3/0033* (2013.01); *A42B 1/24* (2013.01);
(Continued)

(58) Field of Classification Search
CPC ........... A42B 1/24; A42B 1/241; A42B 1/242; A42B 1/08; A42B 1/245; A42B 3/30; A42B 3/32; A42B 3/12; A42B 3/124; A42B 3/14; A41G 3/00; A41G 3/0008; A41G 3/0025; A41G 3/0033; A41G 3/0041; A41G 3/005;
(Continued)

(56) References Cited

U.S. PATENT DOCUMENTS 556,248 A * 3/1896 Boyle .................. A42B 1/24
2/209.13
3,221,340 A * 12/1965 Joffe .................. A42B 3/14
2/417
2006/0200889 A1* 9/2006 Newman .............. A42B 1/12
2/68

FOREIGN PATENT DOCUMENTS

JP    2009-084707 A    4/2009
KR    10-0577734 B1    5/2006
(Continued)

OTHER PUBLICATIONS

International Search Report for PCT/KR2014/011482 dated Mar. 9, 2015.

*Primary Examiner* — Rachel R Steitz
(74) *Attorney, Agent, or Firm* — STIP Law Group, LLC

(57) ABSTRACT

The present invention relates to a hairwear having an auxiliary device for taking the shape of a head or forming a space, and more particularly, to increase a volume for taking the shape of the head of a user or ensure a space for hiding a small electronic device, using an auxiliary device between the head of the user and the hairwear.

18 Claims, 10 Drawing Sheets

(51) Int. Cl.
 *A45D 44/00* (2006.01)
 *A42B 1/24* (2006.01)
 *A61B 5/00* (2006.01)
 *A61B 5/0205* (2006.01)
 *A61B 5/04* (2006.01)

(52) U.S. Cl.
 CPC ............... *A45D 44/00* (2013.01); *A45F 5/00* (2013.01); *A61B 5/0059* (2013.01); *A61B 5/02055* (2013.01); *A61B 5/04001* (2013.01); *A61B 5/4064* (2013.01); *A61B 5/6803* (2013.01); *A45F 2005/002* (2013.01); *A61B 5/0022* (2013.01); *A61B 2560/0242* (2013.01)

(58) Field of Classification Search
 CPC ...... A41G 3/0058; A41G 5/00; A41G 5/0006; A41G 5/0013; A41G 5/0026; A41G 5/0033; A41G 5/0093; A45D 8/38; A45D 8/40; A45D 44/00
 See application file for complete search history.

(56) References Cited

FOREIGN PATENT DOCUMENTS

KR    10-1177258 B1    8/2012
KR    10-2012-0124833 A    11/2012

* cited by examiner

HAIRWEAR HAVING AUXILIARY DEVICE FOR HEAD SHAPING OR SPACE FORMATION

CROSS-REFERENCE TO RELATED APPLICATIONS

This application is the U.S. National Phase under 35 U.S.C. § 371 of International Application No. PCT/KR2014/011482 filed on Nov. 27, 2014, which in turn claims the benefit of Korean Application No. 10-2013-0151906, filed on Dec. 6, 2013, the disclosures of which are incorporated by reference into the present application.

TECHNICAL FIELD

The present invention relates to a hairwear having an auxiliary device for taking the shape of a head or forming a space, and more particularly, to a hairwear having an auxiliary device for shaping a head or forming a space that takes the shape of a head of a user, using an auxiliary device between the user's head and the hairwear, ensures a space for hiding a small electronic device, and keeps the small electronic device in a retainer on the auxiliary device or the hairwear.

BACKGROUND ART

Traditional wigs have been formed in specific shapes by transplanting hairs in a cap-shaped foundation with the entire wig shape maintained by the foundation. However, these wigs have a limit in that they can make hairs abundant, but cannot take the shape of a head.

It has been attempted for users having head shapes with a sunken and flat back to overcome this problem by lifting portion of a wig corresponding to the crown of the heads, but the portion is gradually sunken as time passes.

Korean Patent No. 0844139 (registered on Jun. 30, 2008) by the applicants, as shown in FIG. 1, is characterized by being able to form natural-looking hairs by implanting synthetic hairs or natural hairs in a plurality of hair implant lines at the rear part and by being able to improve a volume-up effect by lifting the hair implant lines with the own hair of a user.

However, this technology has a problem that the volume-up effect is maintained for a short period of time and is gradually decreased by the weight of the hair implant lines or the synthetic hairs or natural hairs in the hair implant lines. Further, it is limited when it is required to achieve a volume-up effect for a predetermined portion of the head of a user.

Further, in the related art, subjects have been temporarily examined in limited spaces such as a research center, a laboratory, or a medical facility in order to examine and study the brains of human, but it is difficult to accomplish various results on natural activities in daily life. That is, since biological signals of subjects were measured with their activities restricted in the related art, it was difficult to measure biological signals in actual daily life.

DISCLOSURE

Technical Problem

The present invention has been made in an effort to provide a hairwear having an auxiliary device for taking the shape of a head and forming a space that can take the shape of a head of a user through a space between or over and under auxiliary devices disposed between the user's head and the hairwear, can hide a small electronic device in the space, and can keep the small device in a retainer on the auxiliary devices or the hairwear.

Technical Solution

An aspect of the present invention provides a hairwear having an auxiliary device for taking the shape of a head and forming a space that includes: a hairwear that is formed in a spherical shape to correspond to the head of a user and has a hairwear bonding portion at a portion or the entire of the area inside an edge; and a first auxiliary device that is formed in a spherical shape to cover a portion or the entire of the inner side of the hairwear, adjacent to the head of the user, and has a first auxiliary bonding portion on a side of a lower edge to be coupled to the hairwear bonding portion and a second auxiliary device that is formed in a spherical shape to cover a portion or the entire of the inner side of the hairwear bonding portion, adjacent to the inner side of the hairwear and has a second auxiliary bonding portion on a side of a lower edge to be coupled to the hairwear bonding portion or the first auxiliary bonding portion, in which a space for increasing a volume for taking the shape of the head of a user or hiding a small electronic device is ensured, through a first space formed between the first auxiliary device and the second auxiliary device, a second space formed between the second auxiliary device and the hairwear, or a third space formed between the first auxiliary device and the head of a user, with the auxiliary devices disposed inside the hairwear.

It is also possible to adjust the height of the first space by vertically adjusting the position where the second auxiliary bonding portion is coupled to the first auxiliary bonding portion.

Another aspect of the present invention provides a hairwear having an auxiliary device for taking the shape of a head and forming a space that includes: a hairwear that is formed in a spherical shape to correspond to the head of a user and has a hairwear bonding portion at a portion or the entire of the area inside an edge; and a first auxiliary device that is formed in a spherical shape to cover a portion or the entire of the inner side of the hairwear, adjacent to the head of the user, and has a first auxiliary bonding portion on a side of a lower edge to be coupled to the hairwear bonding portion, in which a space for increasing a volume for taking the shape of the head of a user or hiding a small electronic device is ensured, through a fourth space formed between the first auxiliary device and the hairwear or a third space formed between the first auxiliary device and the head of a user, with the first auxiliary device disposed inside the hairwear.

The first auxiliary device or the second auxiliary device has a plurality of air holes for ventilation.

The small electronic device includes devices including a chip or a circuit board that can perform wireless communication with devices including a smart phone or a smart glass, and a vibrating device that can provide vibration to a user and a bone conduction vibrating device that converts letters into voice so that user can hear it, when an email or a text is received through the smart phone or the smart glass, or includes a GPS receiver, an ultrasonic converter, a camera, a laser pointer, or a wave signal generator applying wave signals to a brain, or includes devices for measuring biological signals including electroencephalogram, near infrared rays, ballistocardiogram, blood pressure, or body temperature generated around the head of a user, or environmental signals including temperature, humidity, intensity of illumination, or atmospheric pressure around a user.

Advantageous Effects

According to the present invention, since a space is formed by an auxiliary device disposed between the head of a user and a hairwear, it is possible to easily take the shape of the head of a user through the space.

According to the present invention, it is possible to install brain engineering-related small electronic device such as a neuro-biofeedback device that can handle metal diseases and the inclination of a brain of modern people or measure brain waves of users or small-sized sensors capable of checking body temperature or blood pressure, or small-sized devices capable of performing wireless communication with communication devices including a smart phone in a space formed by the auxiliary devices disposed between the head of a user and the hairwear or the retainer formed by the hairwear and the auxiliary devices.

BRIEF DESCRIPTION OF DRAWINGS

The above and other objects, features and advantages of the present invention will be more apparent from the following detailed description taken in conjunction with the accompanying drawings, in which.

REFERENCE SIGNS LIST

Figure 1A:
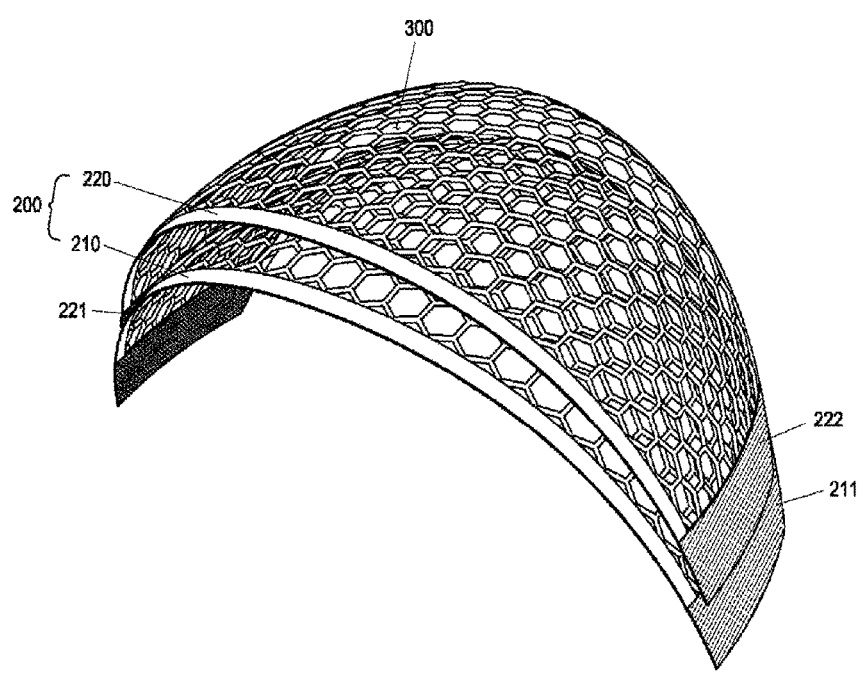
FIGS. 1a and 1b show an embodiment of an auxiliary device applied to the present invention, in which a first auxiliary device and a second auxiliary device that can cover a portion of the inner side of a hairwear are arranged in the same direction and a retainer is provided.

100: Hairwear
110: Front
111: Skin color portion
112: Clip fixing portion
113: Connecting portion
114: Hair implant line
120: Hairwear bonding portion
130: Rear band
200: Auxiliary device
210: First auxiliary device
211: First auxiliary bonding portion
220: Second auxiliary device
221: Second auxiliary bonding portion
300: Air hole
400: Retainer
500: Space
510: First space
520: Second space
530: Third space
540: Fourth space
600: Wig

BEST MODE

Mode for Invention

Hereinafter, exemplary embodiments of the present invention will be described in detail with reference to the accompanying drawings.

The term 'hairwear' used herein is used to show a meaning considering taking the shape of a head, unlike the concept used to supplement pulled hairs in the related art and, for example, includes a function of making it possible to take the shape of the back of a head by increasing the volume of the portion corresponding to the crown of a head above the back of the head and includes a function of ensuring a space for installing a small electronic device used in the brain engineering that have been developed, for example, a device having a function of measuring whether there is a problem with a brain function or studying mental diseases by measuring brain waves. Further, the term 'hairwear' in intended to include the concept enabling a small electronic device including a chip to not only take the shape of a head, but measure a brain function without the small electronic device exposed to the outside.

Further, the 'mall electronic device' described herein means a measuring device disposed in a hairwear, an auxiliary device, and a space defined by the hairwear and the auxiliary device that a user wears, or in a retainer on the hairwear, auxiliary device, or space in order to measure biological signals including electroencephalogram, near infrared rays, ballistocardiogram, blood pressure, or body temperature generated around the head of a user and environmental signals including temperature, humidity, intensity of illumination, or atmospheric pressure around a user. Further, the small electronic device can be connected with sensors through a wire or wirelessly and transmit/receive biological signals and environmental signals, with the sensors for measuring biological signals attached to the head of a user or the sensors for measuring environmental signals hidden in a hairwear.

Further, the small electronic device described herein may include devices including a chip or a circuit board that can perform wireless communication with devices including a smart phone or a smart glass. Further, when an email or a text is received through the smart phone or the smart glass, the small electronic device may include a vibrating device that can provide vibration to a user and a bone conduction vibrating device that converts letters into voice so that user can hear it.

The small electronic device of the present invention may include a GPS receiver, an ultrasonic converter, a camera, or a laser pointer, or a wave signal generator applying wave signals to a brain.

Synthetic hairs or natural hairs are implanted in a skin color part 111 and hair implant lines 114 at the front 110 of a hairwear 100 of the present invention shown in FIGS. 3 and 4, insurance of a space for installing a small electronic device and an effect of taking the shape of a head by increasing a volume, which are main features of the present invention will be more easily understood from the figures showing a state in which the synthetic hairs or natural hairs are not implemented.

A clip fixing portion 112 of the front 110 of the present invention is provided for fixing clips so that the hairwear can be fixed to the hairs over the ears of a user, so clips are fixed inside the clip fixing portion and coupled to the hairs of a user, thereby fixing the hairwear over the user's head. The skin color portion and the clip fixing portion of the front may be continuously formed, but they may be coupled by a connecting portion 13 to improve productivity. A rear band 130 is disposed at the lower end of the hairwear, if necessary, to support the hairwear on the rear end of the user's head.

A hairwear bonding portion 120 according to the present invention is formed at a portion or the entire of the area inside the edge of the hairwear. In the present invention, the edge of the hairwear means the border formed around the hairwear and the portion inside the edge of the hairwear may be the inner side of the rear band having a predetermined width, the portion inside the clip fixing portion, and the portion inside the edge of the skin color portion, and the width may depend on the shape of the hairwear. Since the hairwear bonding portion is formed at a portion or the entire of the area inside the edge of the hairwear, the hairwear bonding portion and a first auxiliary bonding portion of the first auxiliary device and/or a second auxiliary bonding portion of the second auxiliary device can be bonded.

Figure 1B:
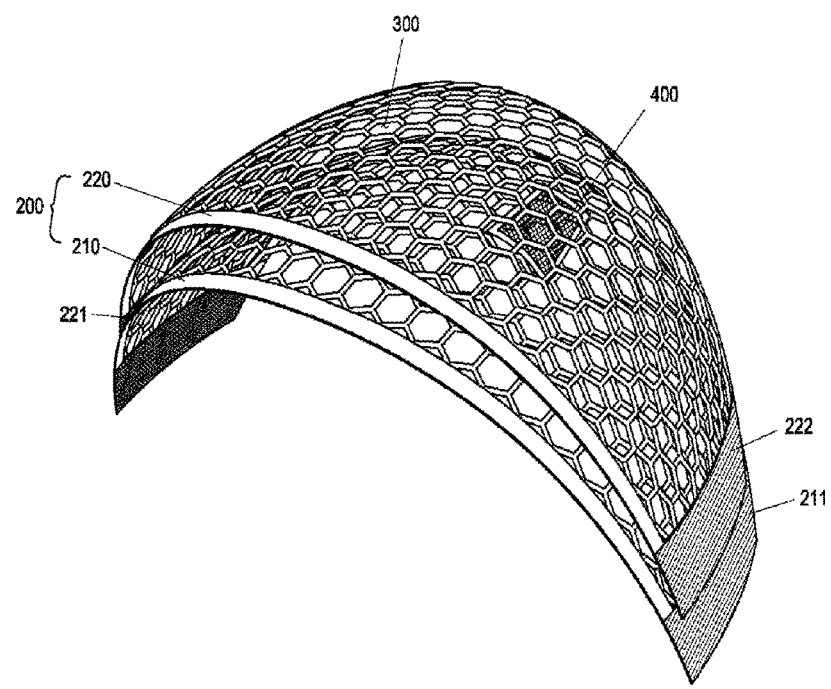

FIG. 1 is a view showing an embodiment of the auxiliary device 200 applied to the present invention, in which a first auxiliary device and a second auxiliary device that can cover a portion of the inner side of a hairwear are arranged in the same direction. FIG. 1a shows the first auxiliary device 210 and the second auxiliary device 220 that are combined and FIG. 1b shows a configuration further including a retainer 400. The first auxiliary device and the second auxiliary device are formed in a spherical shape because they are positioned close to the head of a user. The hairwear 100 that will be described below is also formed in a spherical shape corresponding to the head. The widths A of the first auxiliary device and the second auxiliary device are the same as or smaller than the width H of the hairwear so that the first auxiliary device and the second auxiliary device are not exposed to the outside when the hairwear is worn. FIG. 1 shows an example when the widths of the first auxiliary device and the second auxiliary device are smaller than the width of the hairwear, in which the width of the first auxiliary device or the second auxiliary device may be freely set within the range of 2~20 cmm, and thus they are hidden inside the hairwear. The first auxiliary device and the second auxiliary device may be made of synthetic resin such as plastic that can maintain a shape with predetermined strength to be able to increase a volume of the head shape of a user.

The first auxiliary device and the second auxiliary device are coupled to each other and then combined with the hairwear 100, thereby defining a space 500, and the space 500 can take the shape of a head of a user and hide a small electronic device. That is, a device that can measure brain waves, a sensor that can checks body temperature or blood pressure, and/or a wearable device including a communication function may be reduced in size and disposed in the space. The retainer 400 shown in FIG. 1 is an example of a space for keeping a small electronic device and the size and shape of the retainer may be changed in various ways in accordance with the structure, size, or use of a small electronic device. The small electronic device may be disposed in spaces over and under the first auxiliary device or the second auxiliary device. Further, the retainer may be formed in contact with the top or the bottom of the first auxiliary device or the top or the bottom of the second auxiliary device, or may be formed in contact with the bottom or the top of the hairwear.

A first space 510 is defined between the first auxiliary device 210 and the second auxiliary device 220 in FIG. 1, so when the first space is positioned over the head of a user, the shape of a flat crown portion is taken, and a small electronic device can be installed in the first space.

The first auxiliary device and the second auxiliary device may be combined in various ways, but in the present invention, the first auxiliary bonding portion 211 is formed on a side of the lower edge of the first auxiliary device and the second auxiliary bonding portion 221 is formed on a side of the lower edge of the second auxiliary device. The first auxiliary bonding portion 211 of the first auxiliary device 210 and/or the second auxiliary bonding portion 221 of the second auxiliary device 220 are combined with a hairwear bonding portion 120. The bonding portions may be implemented in various ways, but male and female Velcro tapes may be used, and the first auxiliary bonding portion and the second auxiliary bonding portion may be formed on both of or one of the outer and inner side of the lower edge.

The first auxiliary device and/or the second auxiliary device can be bonded to the hairwear bonding portion 120 formed inside the edge of the hairwear. That is, in the present invention, a stable space can be defined inside the hairwear by selectively combining the first auxiliary device, the second auxiliary device, and/or the hairwear bonding portion, so it is possible to take the shape of a head. The hairwear bonding portion may also be a Velcro tape and male and female parts may be formed to correspond to each other to be easily combined.

In the present invention, it is possible to adjust the height of the first space 510 by adjusting the height where the second auxiliary bonding portion of the second auxiliary device is combined with the first auxiliary bonding portion of the first auxiliary device or the hairwear bonding portion. That is, when the second auxiliary bonding portion is bonded to the upper portion of the first auxiliary bonding portion or the hairwear bonding portion that has a predetermined width, the height of the first space may be increased, and in contrast, when the second auxiliary bonding portion is bonded to the lower portion of the first auxiliary bonding portion or the hairwear bonding portion, the height of the first space may be decreased. Accordingly, the volume-up height is adjusted by adjusting the height where the shape of a head is taken is adjusted, and it is possible to efficiently cope with the size of a small electronic device to be mounted.

Figure 2A:
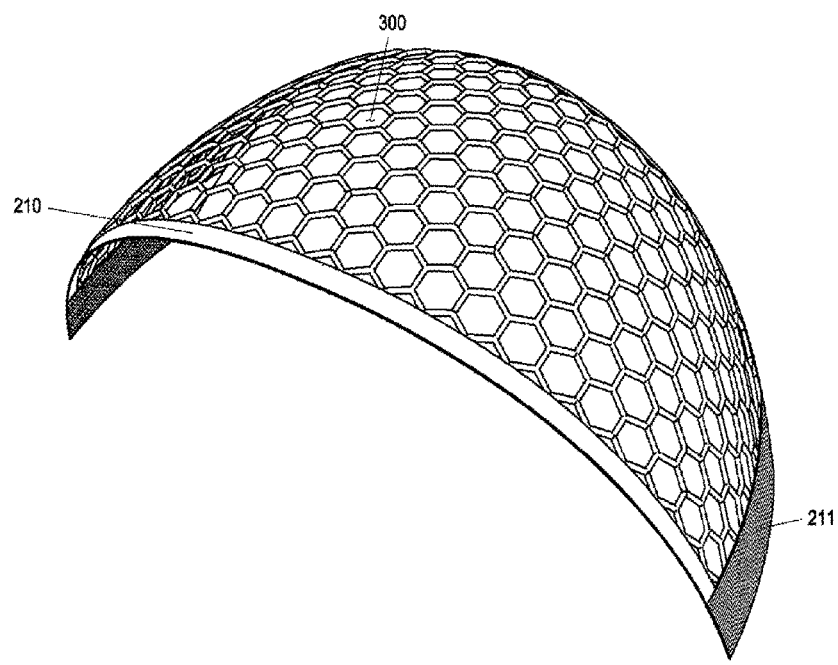
FIGS. 2a and 2b show another embodiment of an auxiliary device applied to the present invention, in which a first auxiliary device that can cover a portion of the inner side of a hairwear and a retainer on the first auxiliary device are provided.
Figure 2B:
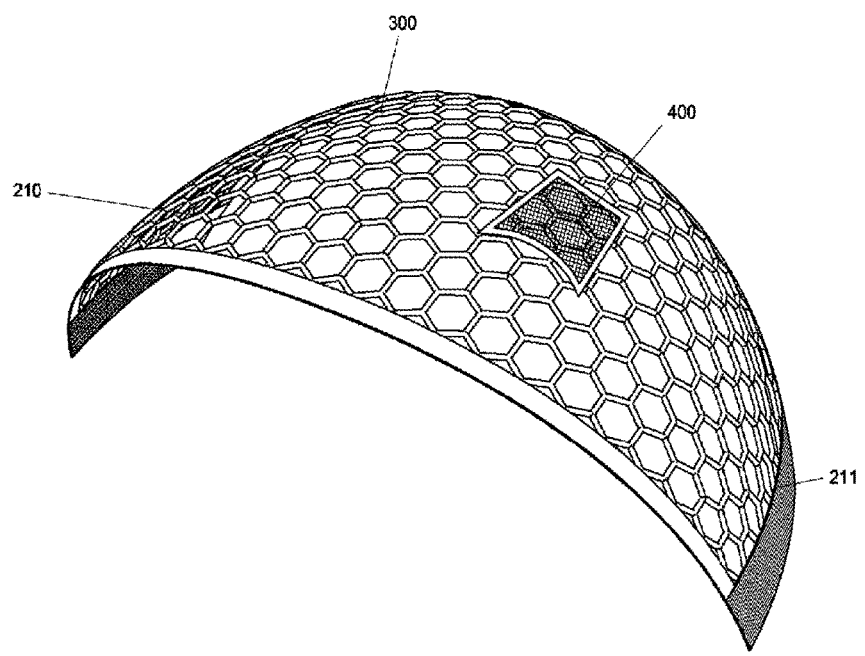

FIG. 2 is a view showing another embodiment of the auxiliary device 200 applied to the present invention, in which a first auxiliary device that can cover a portion of the inner side of a hairwear and a retainer on the first auxiliary device are provided. The first auxiliary device 210 is further shown in FIG. 2a and the retainer 400 disposed on the first auxiliary device is further shown in FIG. 2b, which shows that it is possible to increase a volume and form a space only with the first auxiliary device without the second auxiliary device 220. The first auxiliary bonding portion 211 at a side of the lower edge of the first auxiliary device is coupled to the hairwear bonding portion 120 formed inside the edge of the hairwear, thereby forming a space.

Figure 3A:
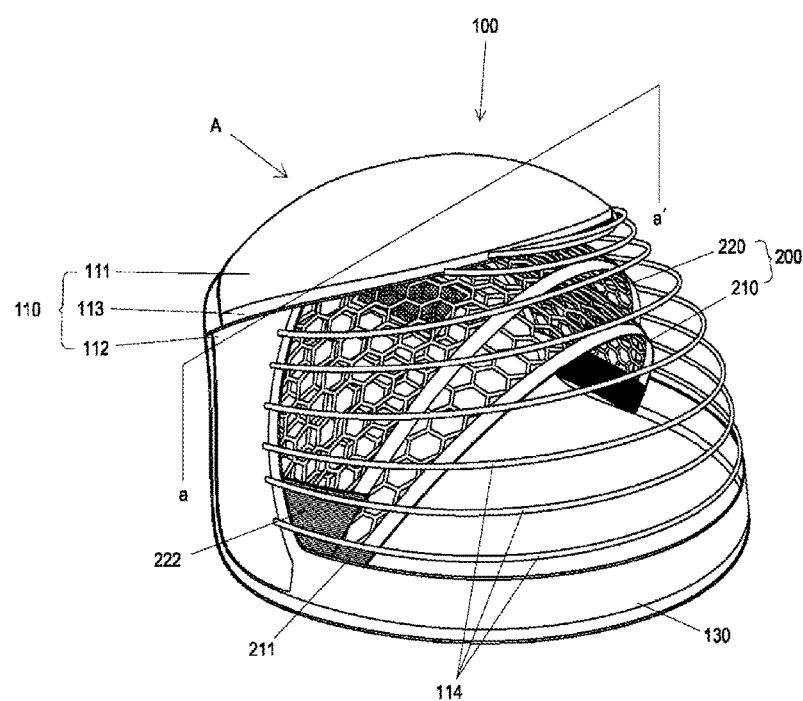
FIGS. 3a and 3b show a case when the auxiliary devices according to the present invention are disposed inside a hairwear.
Figure 3B:
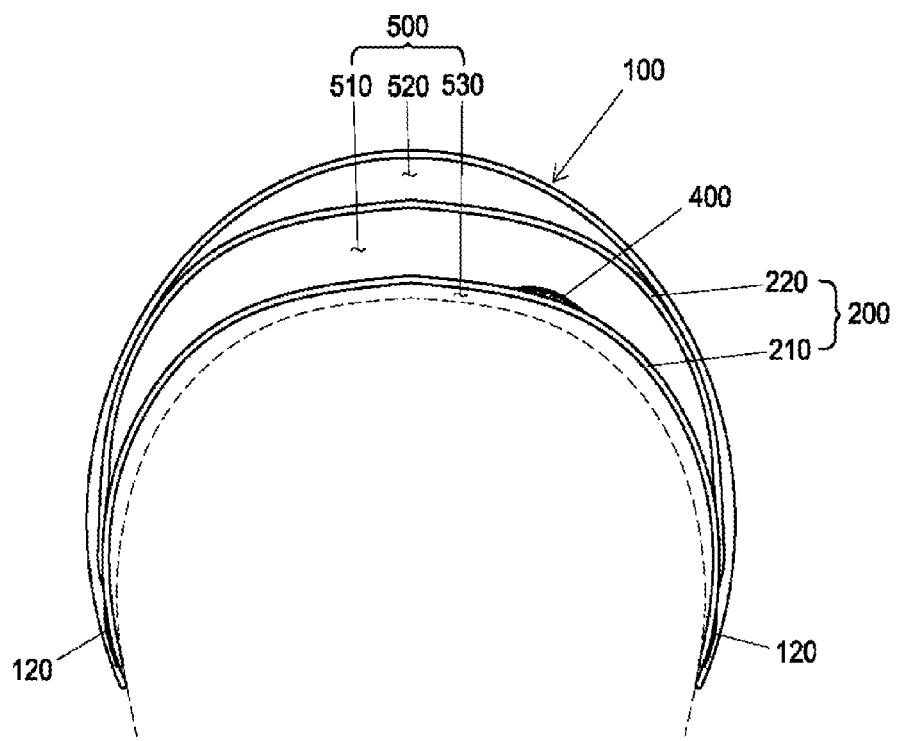

FIG. 3 shows a case when the auxiliary devices according to the embodiment of FIG. 1 are disposed inside a hairwear, in which FIG. 3a shows a first auxiliary device and a second auxiliary device inserted inside a hairwear and FIG. 3b shows a cross-section of FIG. 3a taken along line a-a' when seen in the direction of 'A'. FIG. 3b shows a space formed by auxiliary devices, a hairwear, and the head of a user, in which other components are not shown for the convenience of description and the dotted line under the first auxiliary device indicates the head of a user. Referring to of FIGS. 3a and 3b, it can be seen that together with the first space 510 between the first auxiliary device and the second auxiliary device, a second space 520 is formed between the second auxiliary device and the hairwear, and it can also be seen that a third space 530 is formed between the first auxiliary device and the head of a user.

That is, it is possible to adjust the height of the second space and form the second space by adjusting the position where the first auxiliary bonding portion and/or the second auxiliary bonding portion is bonded to the hairwear bonding portion 120 or adjusting the position where the second auxiliary bonding portion is bonded to the first auxiliary bonding portion. By the structure made by combining the hairwear 100, the first auxiliary device, and the second auxiliary device, spaces are formed at various positions, so volume-up for the head of a user can be easily achieved and a small electronic device can be installed in various spaces. That is, the retainer 400 may be formed in spaces over and under the first auxiliary device or the second auxiliary device, and the retainer may be formed under or over and in contact with the hairwear.

Figure 4A:
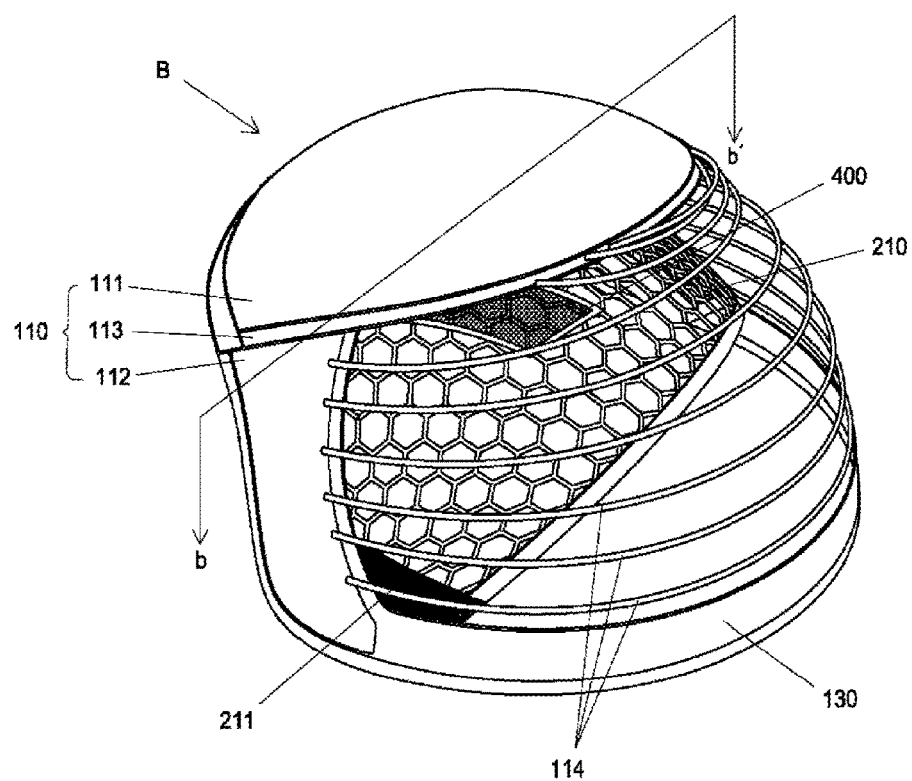
FIGS. 4a and 4b show a case when the first auxiliary device according to the present invention is disposed inside a hairwear.
Figure 4B:
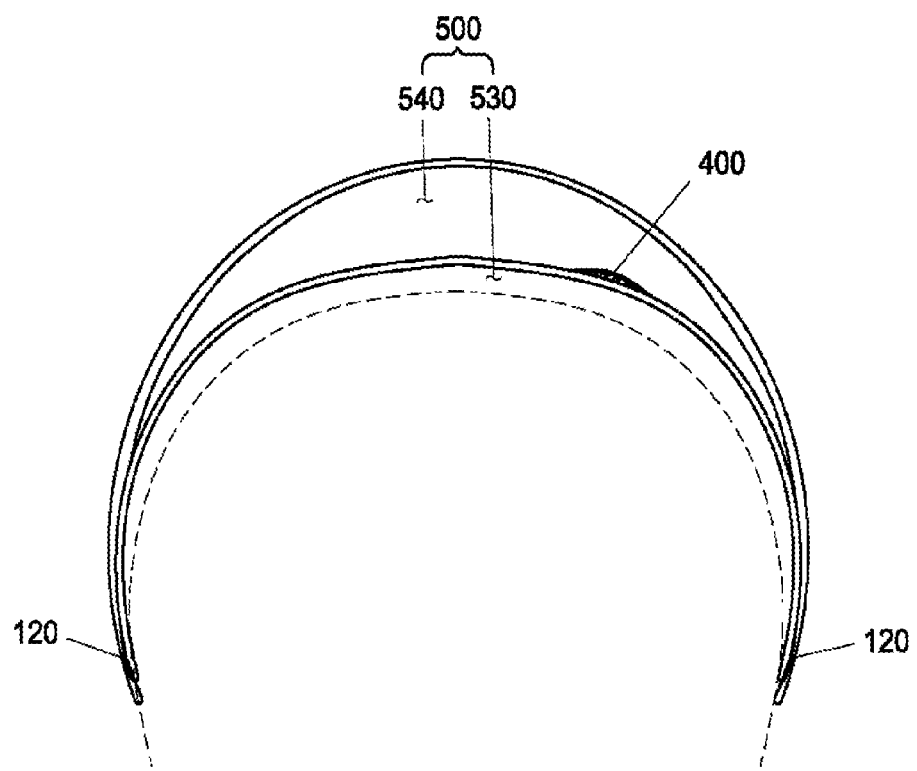

FIG. 4 shows a case when the first auxiliary device according to the embodiment of FIG. 2 is disposed inside a hairwear, in which FIG. 4a shows a first auxiliary device inserted inside a hairwear and FIG. 4b shows a cross-section of FIG. 4a taken along line b-b' when seen in the direction of 'B'. FIG. 4b shows a space formed by auxiliary devices, a hairwear, and the head of a user, in which, similar to FIG. 3b, other components are not shown for the convenience of description and the dotted line under the first auxiliary device indicates the head of a user. Referring to FIGS. 4a and 4b, it can be seen that the first auxiliary bonding portion 211 of the first similar to FIG. 3, is coupled to the hairwear bonding portion 120 formed inside the edge of the hairwear. Referring to FIG. 4, it can be seen that the fourth space 540 is formed between the first auxiliary device 210 and the hairwear 100 and that the third space 530 is formed between the first auxiliary device and the head of a user. In the embodiment shown in FIG. 4, similarly, it is possible to adjust the height of the third space or the fourth space by adjusting the position where the first auxiliary bonding portion 211 of the first auxiliary device is bonded to the hairwear bonding portion 120, so it is possible to easily achieve volume-up for the head of a user and an electronic device may be disposed in the third space or the fourth space or may be disposed in contact with the outer side and the inner side of the hairwear. Even if a small electronic device is disposed in contact with the top of the hairwear, it is not exposed to the outside by hairs.

Figure 5A:
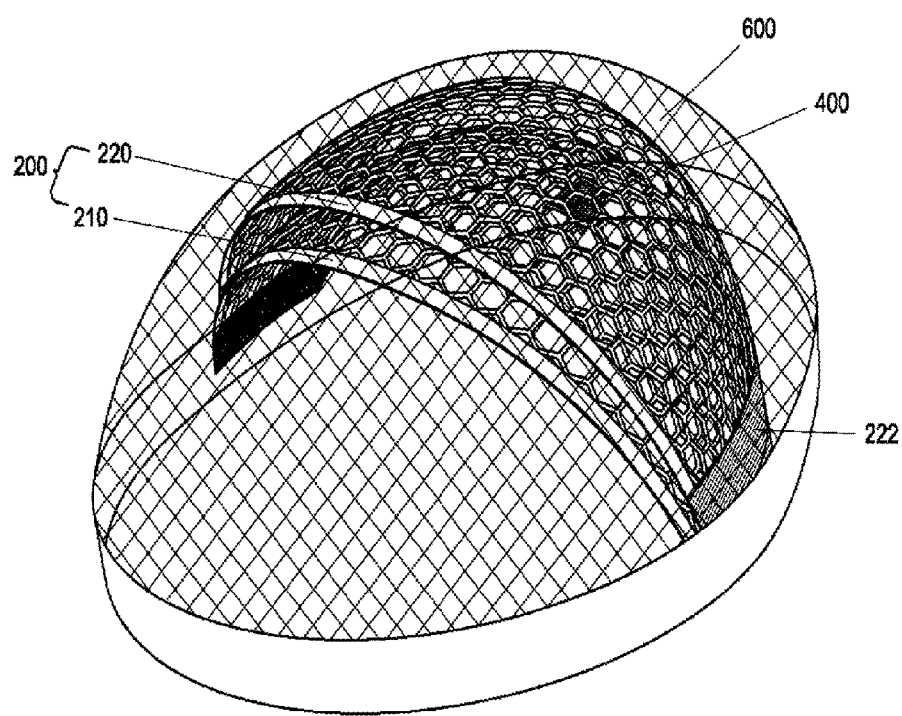
FIGS. 5a and 5b show a case when the auxiliary devices of the present invention are applied to an existing wig.
Figure 5B:
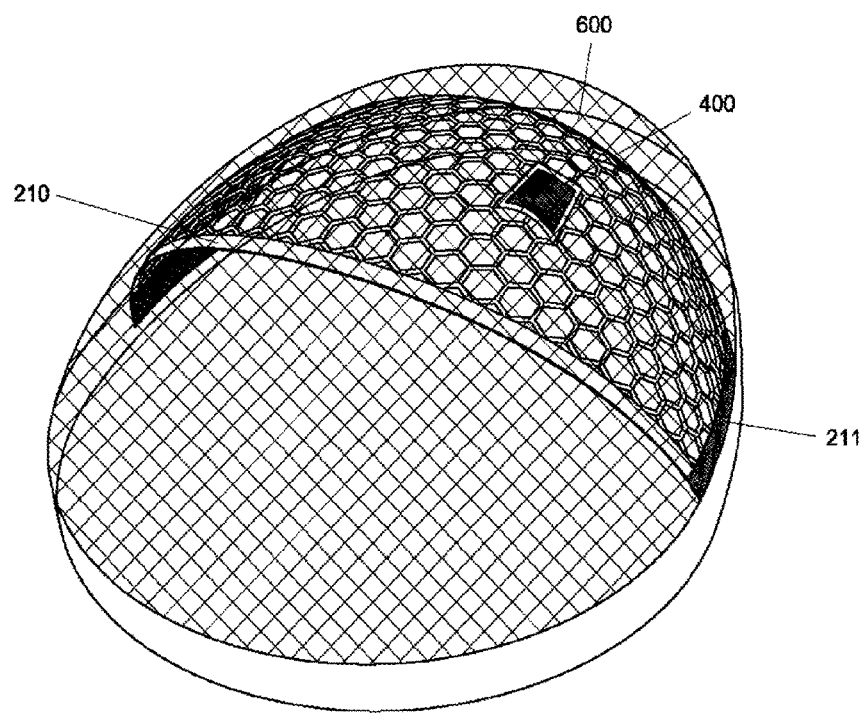

FIG. 5 is a view showing a case when an existing wig is equipped with auxiliary devices of the present invention, unlike the hairwear of the present invention, in which FIG. 5a shows a case when a first auxiliary device and a second auxiliary that cover a portion of the inner side of a wig are disposed inside the wig and FIG. 5b shows a case when a first auxiliary device that can cover a portion of the inner side of a wig is disposed inside the wig. The auxiliary devices of the present invention can be applied to existing wigs. When a wig bonding portion (not shown) is formed at a portion or the entire of the area inside the edge of a wig of the related art and the first auxiliary bonding portion and/or the second auxiliary bonding portion of the present invention is bonded to the wig bonding portion, spaces are formed between the head of a user and the first auxiliary device, between the first auxiliary device and the second auxiliary device, and between the second auxiliary device and the wig, so it is possible to take the shape of a head by increasing a volume and mount a small electronic device in the spaces. A small electronic device may be mounted on the upper or lower portion of the head.

Although auxiliary devices that can cover the inner side of a hairwear or existing wigs are combined with the hairwear or the existing wigs, across the upper portions of both ears of a user in the above embodiments, the auxiliary devices may be combined with the hairwear or the existing wigs from the forehead to the back of the head of a user, and in this case, it is also possible to take the shape of a head of the user by increasing the volume for the crown portion and ensure a space.

Further, though not shown in the figures, the first auxiliary device 210 of the present invention may be formed to cover the entire inner side of the hairwear and the second auxiliary device 220 may be formed to cover a portion of the inner side of the hairwear. On the contrary, the first auxiliary device may be formed to cover a portion of the inner side of the hairwear and the second auxiliary device may be formed to cover the entire inner side of the hairwear.

When the first auxiliary device is formed to cover the entire inner side of the hairwear and the second auxiliary device is formed to cover a portion of the inner side of the hairwear, the second auxiliary device may be disposed in the left and right direction connecting the upper portions of both ears of a user, in the front-rear direction from the forehead to the back of a head, or in any directions, inside the hairwear. On the contrary, when the first auxiliary device is formed to cover a portion of the inner side of the hairwear and the second auxiliary device is formed to cover the entire inner side of the hairwear, the first auxiliary device may be disposed in the left and right direction connecting the upper portions of both ears of a user, in the front-rear direction from the forehead to the back of a head, or in any directions, inside the hairwear.

When the first auxiliary device and/or the second auxiliary device is formed to cover the entire inner side of the hairwear, the first auxiliary bonding portion 211 and/or the second bonding portion 221 may be formed through the area inside the edge of the hairwear or may be formed at a predetermined portion.

When the first auxiliary device or the second auxiliary device are formed to cover the entire inner side of the hairwear, the first auxiliary device or the second auxiliary device may be formed in various shapes such as a circular shape, a +-shape, an X-shape, a T-shape, an H-shape, or a Π-shape. When it is a +-shape, the first auxiliary device is formed in a band shape to cover the entire inner side of the hairwear, thereby forming a space. In this case, a space is ensured with the head of a user supported, and a small electronic device can be mounted on the band-shaped upper surface or lower surface.

As described above with reference to FIGS. 1 to 5, when the first auxiliary device of the second auxiliary device used in the present invention is formed to cover a portion of the inner side of the hairwear, the width may be freely set, but may be set within the range of 2~10 cmm not to be exposed to the outside when a user wears the hairwear. When the first auxiliary device and the second auxiliary device are both formed to cover a portion of the inner side of the hairwear, they may be positioned in the same way in the left-right direction connecting the upper portions of both ears of a user, in the front-rear direction from the forehead and the back of the head, or in any direction inside the hairwear through the hairwear bonding portion formed on the rear band inside the hairwear and/or inside the skin color portion of the front, or they may be positioned in different directions.

With only the first auxiliary device disposed while the second auxiliary device is omitted inside the hairwear, the first auxiliary device may be formed to cover the entire inner side of the hairwear, and when the first auxiliary device is provided to cover a portion of the hairwear, the first auxiliary device may be positioned in the left-right direction connecting the upper portions of both ears of a user, in the front-rear direction from the forehead and the back of the head, or in any direction.

Referring to FIGS. 1 and 2, it can be seen that a plurality of air holes 300 is formed in the auxiliary devices of the present invention. External device can flow to the head of a user through the air holes, heat or sweat from the head of the user can be smoothly discharged.

Though not shown in the figures, according to the present invention, a small electronic device may be disposed on the outer side or the inner side of a hairwear of a wig of the related art. When a retainer is formed on the outer side or the inner side of a hairwear of a wig of the related art and then a small electronic device may be placed in the retainer. The hairwear of the wig of the related art may be used as a unit for measurement in the brain engineering through the small electronic device. Further, although two or one auxiliary device was exemplified, if necessary, three or more auxiliary devices may be provided, and they may be combined in the way of combining two auxiliary devices.

According to the present invention, since a space is formed by the auxiliary devices disposed between the head of a user and a hairwear, it is possible to easily take the shape of the head of the user through the space. Further, it is possible to install brain engineering-related small electronic device such as a neuro-biofeedback device that can handle metal diseases and the inclination of a brain of modern people or measure brain waves of users or small-sized sensors capable of checking body temperature or blood pressure and/or small-sized communication devices in a space formed by the auxiliary devices disposed between the head of a user and the hairwear or the retainer formed by the hairwear and the auxiliary devices.

Although embodiments of the present invention were described above, the spirit of the present invention is not limited thereto, changes and modifications substantially equivalent to the embodiment of the present invention should be construed as being included in the scope of the present invention, and the prevent invention may be changed in various ways within the scope of the present invention by those skilled in the art.

INDUSTRIAL APPLICABILITY

The present invention relates to a hairwear having an auxiliary device for shaping a head or forming a space that takes the shape of a head of a user, using an auxiliary device between the user's head and the hairwear, ensures a space for hiding a small electronic device, and keeps he small electronic device in a housing on the auxiliary device or the hairwear.

The invention claimed is:

1. A hairwear device having an auxiliary device for taking the shape of a head and forming a space, comprising:
   a hairwear that is formed in a spherical shape to correspond to the head of a user and has a hairwear bonding portion at a portion or the entire of the area inside an edge;
   a first auxiliary device that is formed in a spherical shape to cover a portion or the entire portion of an inner side of the hairwear, adjacent to the head of the user, and has a first auxiliary bonding portion on a side of a lower edge to be coupled to the hairwear bonding portion; and
   a second auxiliary device that is formed in a spherical shape to cover a portion or the entire of the inner side of the hairwear bonding portion, adjacent to the inner side of the hairwear and has a second auxiliary bonding portion on a side of a lower edge to be coupled to the hairwear bonding portion or the first auxiliary bonding portion,
   wherein the hairware device contains a first space formed between the first auxiliary device and the second auxiliary device, a second space formed between the second auxiliary device and the hairwear, or a third space formed between the first auxiliary device and the head of a user, with the first and the second auxiliary devices disposed inside the hairwear,
   wherein the first auxiliary bonding portion and the second auxiliary bonding portion are structurally separate from one another, and
   wherein the first and the second auxiliary devices can adjust the height of the first space by vertically adjusting the position where the second auxiliary bonding portion is coupled to the first auxiliary bonding portion.

2. The hairwear device as claimed in claim 1, wherein the first and the second auxiliary devices have a plurality of air holes for ventilation.

3. The hairwear device as claimed in claim 1, wherein the first auxiliary device or the second auxiliary device has a retainer for keeping a small electronic device.

4. The hairwear device as claimed in claim 1, the hairware device further comprises a small electronic device, wherein the small electronic device includes all or some of a GPS receiver, an ultrasonic converter, a camera, a laser pointer, or a wave signal generator applying wave signals to a brain.

5. The hairwear device as claimed in claim 1, the hairware device further comprises a small electronic device, wherein the small electronic device includes all or some of devices for measuring biological signals including electroencephalogram, near infrared rays, ballistocardiogram, blood pressure, or body temperature generated around the head of a user, or environmental signals including temperature, humidity, intensity of illumination, or atmospheric pressure around a user.

6. The hairwear device as claimed in claim 1, wherein the first auxiliary device is formed to cover the entire inner side of the hairwear and the second auxiliary device is formed to cover a portion of the inner side of the hairwear.

7. The hairwear device as claimed in claim 6, wherein the second auxiliary device is positioned in the left-right direction connecting the upper portions of both ears of a user, in the front-rear direction from the forehead and the back of the head, or in any direction inside the hairwear.

8. The hairwear device as claimed in claim 1, wherein the first auxiliary device is formed to cover a portion of inner side of the hairwear and the second auxiliary device is formed to cover the entire inner side of the hairwear.

9. The hairwear device as claimed in claim 1, wherein the first and the second auxiliary devices have a plurality of air holes for ventilation.

10. The hairwear device as claimed in claim 1, wherein the first auxiliary device is formed to cover the entire inner side of the hairwear and the second auxiliary device is formed to cover a portion of the inner side of the hairwear.

11. The hairwear device as claimed in claim 10, wherein the second auxiliary device is positioned in the left-right direction connecting the upper portions of both ears of a user, in the front-rear direction from the forehead and the back of the head, or in any direction inside the hairwear.

12. The hairwear device as claimed in claim 1, wherein the first auxiliary device is formed to cover a portion of inner side of the hairwear and the second auxiliary device is formed to cover the entire inner side of the hairwear.

13. A hairwear device having an auxiliary device for taking the shape of a head and forming a space comprising:
    a hairwear that is formed in a spherical shape to correspond to the head of a user and has a hairwear bonding portion at a portion or the entire of the area inside an edge; and
    a first auxiliary device that is formed in a spherical shape to cover a portion or the entire of an inner side of the hairwear, adjacent to the head of the user, and has a first auxiliary bonding portion on a side of a lower edge to be coupled to the hairwear bonding portion,
    wherein the hairware device contains a fourth space formed between the first auxiliary device and the hairwear or a third space formed between the first auxiliary device and the head of the user, with the first auxiliary device disposed inside the hairwear,
    wherein the first auxiliary bonding portion and the hairwear bonding portion are structurally separate from one another, and
    wherein the first auxiliary device has a plurality of air holes for ventilation.

14. The hairwear device as claimed in claim 13, wherein the first auxiliary device has a retainer for keeping a small electronic device.

15. The hairwear device as claimed in claim 13, the hairware device further comprises a small electronic device, wherein the small electronic device includes some or all of a chip or a circuit board that can perform wireless communication with devices including a smart phone or a smart glass, and a vibrating device that can provide vibration to a user and a bone conduction vibrating device that converts letters into voice so that user can hear it, when an email or a text is received through the smart phone or the smart glass.

16. The hairwear device as claimed in claim 13, the hairware device further comprises a small electronic device, wherein the small electronic device includes all or some of a GPS receiver, an ultrasonic converter, a camera, a laser pointer, or a wave signal generator applying wave signals to a brain.

17. The hairwear device as claimed in claim 13, the hairware device further comprises a small electronic device, wherein the small electronic device includes all or some of devices for measuring biological signals including electroencephalogram, near infrared rays, ballistocardiogram, blood pressure, or body temperature generated around the head of a user, or environmental signals including temperature, humidity, intensity of illumination, or atmospheric pressure around a user.

18. A hairwear device having an auxiliary device for taking the shape of a head and forming a space, comprising:
    a hairwear that is formed in a spherical shape to correspond to the head of a user and has a hairwear bonding portion at a portion or the entire of the area inside an edge;
    a first auxiliary device that is formed in a spherical shape to cover a portion or the entire portion of an inner side of the hairwear, adjacent to the head of the user, and has a first auxiliary bonding portion on a side of a lower edge to be coupled to the hairwear bonding portion; and
    a second auxiliary device that is formed in a spherical shape to cover a portion or the entire of the inner side of the hairwear bonding portion, adjacent to the inner side of the hairwear and has a second auxiliary bonding portion on a side of a lower edge to be coupled to the hairwear bonding portion or the first auxiliary bonding portion,
    wherein the hairware device contains a first space formed between the first auxiliary device and the second auxiliary device, a second space formed between the second auxiliary device and the hairwear, or a third space formed between the first auxiliary device and the head of a user, with the first and the second auxiliary devices disposed inside the hairwear,
    wherein the first auxiliary bonding portion and the second auxiliary bonding portion are structurally separate from one another, and
    wherein the hairware device has a small electronic device, wherein the small electronic device includes some or all of a chip or a circuit board that can perform wireless communication with devices including a smart phone or a smart glass, and a vibrating device that can provide vibration to a user and a bone conduction vibrating device that converts letters into voice so that user can hear it, when an email or a text is received through the smart phone or the smart glass.

* * * * *